(12) United States Patent
Cook (10) Patent No.: US 6,705,321 B2
(45) Date of Patent: *Mar. 16, 2004

(54) LARYNGEAL MASK ADAPTER (76) Inventor: Daniel J. Cook, 1167 Hillside Dr., St. Louis, MO (US) 63117-3117

(*) Notice: Subject to any disclaimer, the term of this patent is extended or adjusted under 35 U.S.C. 154(b) by 141 days.

This patent is subject to a terminal disclaimer.

(21) Appl. No.: 09/829,157

(22) Filed: Apr. 9, 2001

(65) Prior Publication Data
US 2001/0017135 A1 Aug. 30, 2001

Related U.S. Application Data (60) Continuation-in-part of application No. 09/179,928, filed on Oct. 27, 1988, now Pat. No. 6,422,239, which is a division of application No. 08/843,631, filed on Apr. 10, 1997, now Pat. No. 5,937,860.

(51) Int. Cl.⁷ ............................................. A61M 16/00
(52) U.S. Cl. .................... 128/207.15; 128/207.14; 128/200.26; 128/DIG. 26
(58) Field of Search ................. 128/207.15, 207.14, 128/200.26, DIG. 26

(56) References Cited

U.S. PATENT DOCUMENTS

| | | | | |
|---|---|---|---|---|
| 3,734,100 A | | 5/1973 | Walker et al. ............ 128/351 |
| 4,146,034 A | * | 3/1979 | Gupta ...................... 128/207.14 |
| 4,509,514 A | | 4/1985 | Brain ....................... 128/207.15 |
| 4,863,439 A | * | 9/1989 | Sanderson ................ 604/264 |
| 4,995,388 A | * | 2/1991 | Brain ....................... 128/207.15 |
| 5,024,220 A | * | 6/1991 | Holmgreen et al. ..... 128/207.18 |
| 5,277,178 A | | 1/1994 | Dingley ................... 128/200.26 |
| 5,282,464 A | | 2/1994 | Brain ....................... 128/207.15 |
| 5,303,697 A | * | 4/1994 | Brain ....................... 128/200.26 |
| 5,392,774 A | | 2/1995 | Sato ........................ 128/207.15 |
| 5,529,582 A | | 6/1996 | Fukuhara ................. 606/205 |
| 5,545,048 A | * | 8/1996 | Maeda ..................... 439/273 |
| 5,569,222 A | * | 10/1996 | Haselhorst et al. ..... 604/533 |
| 5,623,921 A | | 4/1997 | Kinsinger et al. ...... 128/200.26 |
| 5,632,271 A | | 5/1997 | Brain ....................... 128/207.15 |
| 5,643,174 A | * | 7/1997 | Yamamoto et al. ..... 600/114 |
| 5,653,231 A | | 8/1997 | Bell ......................... 128/207.16 |
| 5,682,880 A | * | 11/1997 | Brain ....................... 128/207.15 |
| 5,713,348 A | * | 2/1998 | Pell .......................... 128/202.27 |
| 5,772,643 A | * | 6/1998 | Howell et al. ........... 604/533 |
| 5,787,879 A | * | 8/1998 | Gibson .................... 128/202.27 |
| 5,878,745 A | * | 3/1999 | Brain ....................... 128/207.15 |
| 5,937,860 A | * | 8/1999 | Cook ....................... 128/207.15 |

* cited by examiner

Primary Examiner—Weilun Lo
Assistant Examiner—Darwin Erezo
(74) Attorney, Agent, or Firm—Ahaji K. Amos (57) ABSTRACT A laryngeal mask of the type used to facilitate lung ventilation and the insertion of endotracheal tubes or related medical instruments through a patient's laryngeal opening as used during general anesthesia, intensive care, or critical patient care. The mask includes an inflatable positioning shield formed to fit within a patients oropharynx and seal around the circumference of the laryngeal opening, the shield having an inflatable annular toroid peripheral portion, a contoured rear portion, and a recessed front. The mask also includes a flexible respiratory tube having a proximal end lumen, a gently curved tubular body of sufficient size to permit passage of endotracheal tubes, and related medical instruments, and a distal end passing through and secured to the proximal edge of the annular toroid peripheral portion. The distal end of the tube terminates at the distal lumen within the recessed front of the inflatable positioning shield such that tubes and instruments passing through the flexible respiratory tube will be directed into the laryngeal opening. An adapter for use with medical devices is also disclosed. The adapter includes a body, a first end, a second end, and a passage therethrough wherein one end has an elliptical cross-section.

16 Claims, 5 Drawing Sheets

LARYNGEAL MASK ADAPTER

CROSS-REFERENCE TO RELATED APPLICATIONS

The present application is a continuation-in-part of U.S. application Ser. No. 09/179,928 filed on Oct. 27, 1988 now U.S. Pat. No. 6,422,239, which is a divisional of Ser. No. 08/843,631 filed on Apr. 10, 1997 now U.S. Pat. No. 5,937,860 issued on Aug. 17, 1999.

STATEMENT REGARDING FEDERALLY SPONSORED RESEARCH OR DEVELOPMENT

Not applicable.

BACKGROUND OF THE INVENTION

This invention relates to an artificial airway device designed to facilitate lung ventilation and the insertion of endotracheal tubes or related medical instruments into the laryngeal opening of an unconscious patient.

In general, laryngeal masks allowing for both rapid lung ventilation and the insertion of medical instruments and tubes into the laryngeal openings of patients have been described in patents such as Brain, U.S. Pat. No. 4,509,514. Consisting of two essential parts, a breathing tube and an inflatable mask, these instruments or devices are inserted blindly into a patient's throat, and when properly positioned, terminate at the laryngeal opening. A seal is then formed around the circumference of the laryngeal opening by the inflation of a ring-like structure located on the front of the mask. Inflation of the ring exerts pressure against both the front and rear portions of the oropharynx, securing the device in place such that the laryngeal opening is positioned within a recessed cavity in the mask face. Extending from a point external to the oral cavity, the flexible breathing tube terminates within the recessed cavity, aligned axially with the laryngeal opening. The positioning of the flexible breathing tube allows the passage of small diameter endotracheal tubes or related medical instruments into the laryngeal opening, in addition to allowing for lung ventilation.

It has been discovered that laryngeal masks of the above-mentioned type have superior performance if its associated respiratory tube has an elliptical cross-section. This shape, however, can present a problem, since medical tubing (including the tubing for connecting to respiratory tubes) is typically circular in cross-section. This mismatch can create connection problems, leakage problems or even disconnections.

SUMMARY OF THE INVENTION

Among the several objects and advantages of the present invention include:

The provision of a new and improved laryngeal mask for the facilitation of lung ventilation and the insertion of endotracheal tubes and related medical instruments into the laryngeal opening;

The provision of the aforementioned laryngeal mask which includes an adapter for connection to medical instruments or devices, wherein the adapter includes at least one end that has an elliptical cross-section; and The provision of the aforementioned laryngeal mask which includes an adapter for connection to medical instruments or devices, which includes raised ribs disposed circumferentially about the adapter for positioning of tubing.

Other objects will be in part apparent and in part pointed out hereinafter.

Briefly, a laryngeal mask of the present invention includes an inflatable positioning shield formed to fit within a patient's oropharynx and seal around the circumference of the laryngeal opening. The shield has a recessed front to securely surround the trachea after inflation, preventing lateral movement of the laryngeal mask. The mask also includes a flexible respiratory tube having a proximal end, a distal end, a gently curved tubular body of sufficient size to permit passage of endotracheal tubes, and related medical instruments, and a lumen therethrough terminating within the recessed front of the inflatable positioning shield such that tubes and instruments passing through the flexible respiratory tube are directed into the laryngeal opening. The flexible respiratory tube has an elliptical cross-section, facilitating insertion of the laryngeal mask through the oral cavity. An adapter is coupled to the proximal end of the respiratory tube for connection of medical instruments or devices, the adapter including a body having a first end, a second end and a passage therethrough. The first end of the adapter has an elliptical cross-section for communication with the lumen of the flexible respiratory tube, and said second end has a cross-section which differs from the cross-section of the first end.

In a second aspect of the present invention, a laryngeal mask includes an inflatable positioning shield formed to fit within a patient's oropharynx and seal around the circumference of the laryngeal opening, said shield having an inflatable annular toroid peripheral portion, a contoured rear portion, and a distal front portion. The mask also includes a flexible respiratory tube having proximal and distal ends, and a lumen therebetween defined by a gently curved tubular body. The distal end of the respiratory tube terminates within the front of the inflatable positioning shield such that tubes and instruments passing through the flexible respiratory tube are directed into the laryngeal opening. The flexible respiratory tube has an elliptical cross-section facilitating insertion of the laryngeal mask through the oral cavity. An adapter is coupled to the proximal end of said respiratory tube for connection of medical instruments or devices, said adapter comprising a body having a first end that has an elliptical cross-section, a second end that has a circular cross-section, a wall member disposed substantially centrally between said first end and said second end, and a passage therethrough.

In a third aspect of the present invention an adapter of the type suitable for connection of medical instruments or devices includes a body having a first end, a second end, and a passage therethrough. The first end has an elliptical cross-section for connection of tubing having an elliptical cross-section, and the second end has a cross-section that differs from the cross-section of the first end.

In a fourth aspect of the present invention, an adapter of the type suitable for connection of medical instruments or devices includes a body having a first end, a second end, a wall member disposed substantially centrally between said first end and said second end, and a passage therethrough. The first end has an elliptical cross-section for connection of tubing of a first kind and at least one raised rib disposed circumferentially around an external portion of said first end. The second end has a circular cross-section for attachment of tubing of a second kind.

BRIEF DESCRIPTION OF THE DRAWINGS

In the drawings.

Corresponding reference numerals indicate corresponding parts throughout the several figures of the drawings.

DESCRIPTION OF THE PREFERRED EMBODIMENTS

The following detailed description illustrates the invention by way of example and not by way of limitation.

Figure 1:
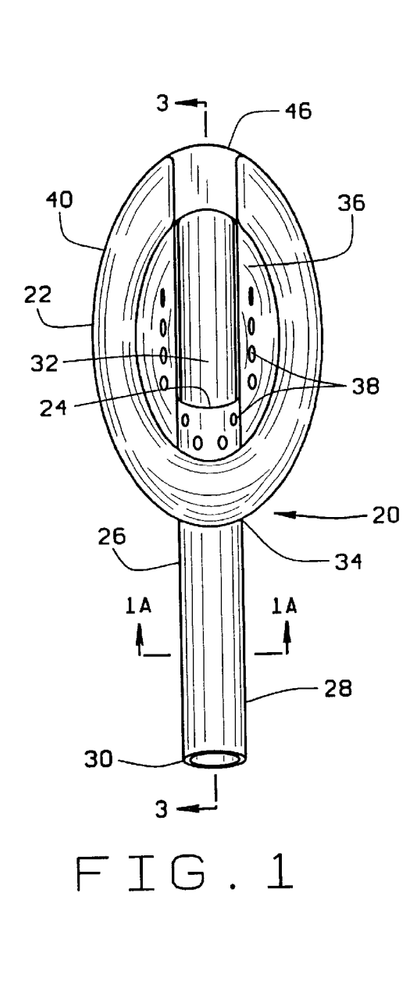
FIG. 1 is a top view of the laryngeal mask illustrating the flexible breathing tube and the inflatable positioning shield.
Figures 1A, 2:
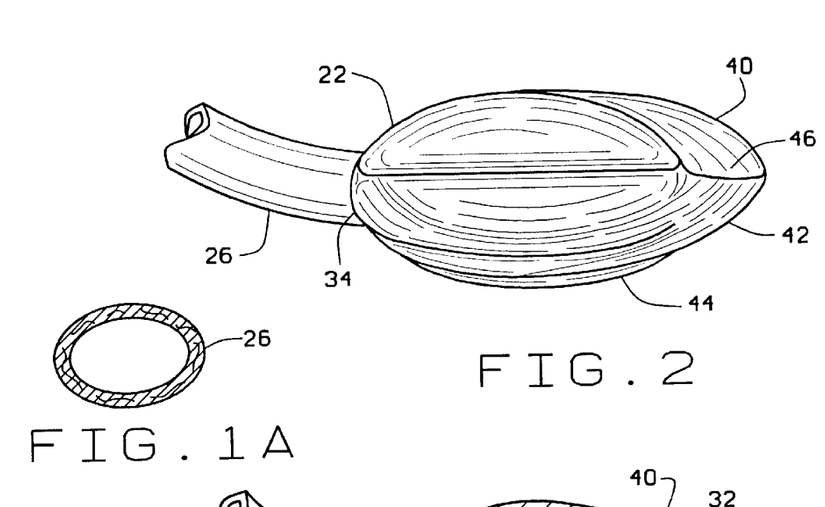
FIG. 1A is a cross-sectional view taken along line 1A—1A in FIG. 1.
FIG. 2 is a side view of the inflatable positioning shield after inflation.
Figure 3:
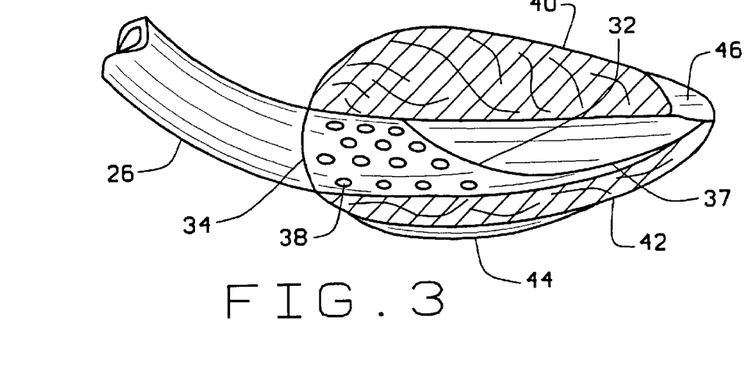
FIG. 3 is a sectional view of the inflatable positioning shield after inflation, taken along line 3—3 of FIG. 1.
Figure 7:
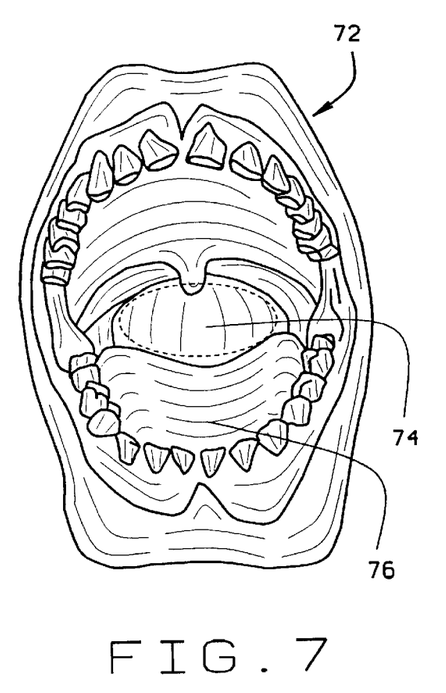
FIG. 7 is an artists rendition of a patient's oral cavity, illustrating the elliptical nature of the opening into the oropharynx region.

Referring to the drawings, and particularly FIGS. 1–3 inclusive, a removable laryngeal mask is shown generally at 20. The laryngeal mask 20 comprises an inflatable positioning shield 22 secured to the distal end 24 of a respiratory tube 26, forming a smooth arcuate curve as shown in FIG. 3. Composed of a flexible silicone-rubber polymer, respiratory tube 26 has an elliptical cross-section (see FIG. 1A), approximating, for ease of insertion, the shape of the human throat shown in FIG. 7. Capable of spreading radially, respiratory tube 26 can accommodate the passage of cuffed endotracheal tubes and related medical instruments or devices up to 8.0 French in diameter. The length of respiratory tube 26 is such that when the laryngeal mask 20 is properly positioned for use within the oropharynx, the attachment end 28 of respiratory tube 26 is located exterior to the oral cavity. The attachment end 28 of the respiratory tube 26 terminates in an unobstructed proximal lumen 30, providing a direct pathway through the respiratory tube 26 to the distal end 24 and distal lumen 32. In alternative embodiments, the attachment end 28 may be fitted with adapters or connectors (see FIGS. 14 and 15A–C) suitable for connection to a variety of medical instruments or devices, for example, lung ventilation machines.

The distal end 24 is the continuous portion of respiratory tube 26 which has passed through an airtight peripheral seal 34 at the rear of the inflatable positioning shield 22, and into the shield recess 36. The distal end 24 terminates at an angle to its length, forming the elongated elliptically shaped distal lumen 32 open to the interior of the shield recess 36. The elongated lower surface of the distal end forms the shield support 37, and provides a semi-rigid structure onto which the positioning shield 22 is secured. Numerous ventilation lumen 38 perforate the distal end 24 to provide alternate airways in the event the distal lumen 32 becomes obstructed during patient lung ventilation. The ventilation lumen 38 prevent the formation of a pressure differential between the shield recess 36 and flexible respiratory tube 26. Absent a pressure differential, any object obstructing the distal lumen 32 will not become inextricably lodged within the distal end 24.

Figure 4:
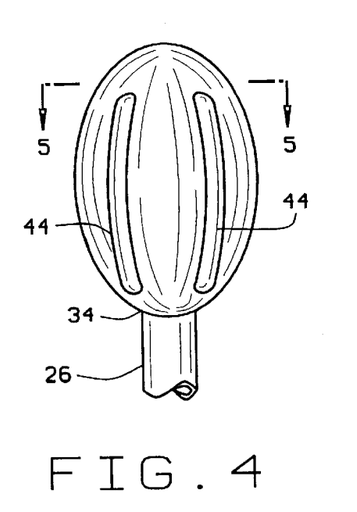
FIG. 4 is bottom view of the inflatable positioning shield.
Figure 5:
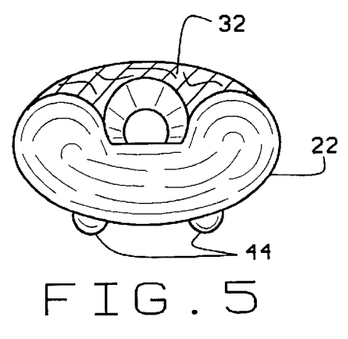
FIG. 5 is a sectional view of the inflatable positioning shield after inflation, taken along line 5—5 of FIG. 4, illustrating the recessed front of the positioning shield and the unobstructed distal lumen of the flexible breathing tube.
Figure 6:
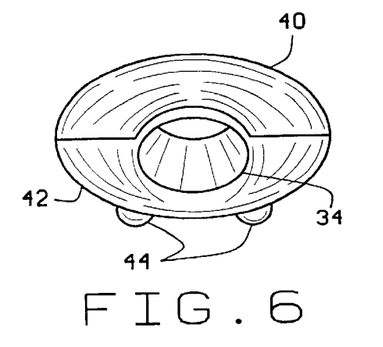
FIG. 6 is a rear view of the inflatable positioning shield after inflation, with the flexible breathing tube removed.

The inflatable positioning shield 22 is composed of a wedge-shaped toroid 40, and a pliable molded posterior base 42. Inflation of the toroid 40 is accomplished by means of a conventional inflation device (not shown), forming an ovoid shape conforming to the approximate available space in the oropharynx region. The posterior base is secured longitudinally in an airtight manner to the lower surface of the shield support 37. The posterior base 42 forms an elongated and tapered hemisphere, best seen in FIGS. 2–4. Two semi-rigid raised runners 44 formed of molded silicone rubber are positioned longitudinally parallel to each other along the lower surface of the posterior base 42. During insertion of the laryngeal mask 20, the raised runners 44 guide the placement of the inflatable positioning shield 22, aid in preventing lateral movement by fitting to the rear anatomy of the oropharynx region, and facilitate placement by decreasing drag. In fluid communication with the posterior base 42, the annular toroid 40 is secured to the peripheral upper surface of the posterior base 42, and inflates simultaneously to form the shield recess 36. A tracheal notch 46 is formed in the portion of the annular toroid 40 traversing the front of the inflatable positioning shield 22, best seen in FIG. 1. The tracheal notch 46 surrounds the trachea after proper positioning and inflation of the laryngeal mask 20, preventing lateral movement and creating a better airtight fit with the trachea.

During use, the laryngeal mask 20 is inserted through the oral cavity with the annular toroid 40 fully deflated. The smooth arcuate curve of the combined respiratory tube 26 and positioning shield 22 ensures proper positioning of the laryngeal mask 20 within the anatomy surrounding the laryngeal opening. Upon proper positioning, as determined by a resistance to further forward motion, the annular toroid 40 is inflated as described above. When fully inflated, the annular toroid 40 exerts sufficient pressure against the structures of the oropharynx to form a tight seal surrounding the laryngeal opening. Positioned within the shield recess 36, the distal lumen 32 is axially aligned with the laryngeal opening, permitting positive lung ventilation to be performed, or allowing endotracheal tubes or related medical instruments inserted through the respiratory tube 26 to exit the distal lumen 32, directly aligned for passage into the laryngeal opening.

Removal of the laryngeal mask 20 is normally the reverse of the insertion procedure described above. In some situations, however, it is desired to remove the laryngeal mask 20 without simultaneously removing or dislodging endotracheal tubes or related medical instruments or devices passing through respiratory tube 26 into the laryngeal opening. Referring generally to FIGS. 8–13, removal of the laryngeal mask 20 under such circumstances is facilitated by means of a tube retainer, shown generally at 48.

Tube retainer 48 comprises a connection adapter 50, a stylet rod 52, and an endcap 68. Connection adapter 50 is composed of a soft semi-rigid material forming a truncated conical structure having four equidistantly positioned longitudinal ventilation grooves 56. Each ventilation groove 56 permits the passage of air around the connection adapter 50 after insertion within an endotracheal tube as shown generally in FIGS. 11–13. The exterior surface of connection adapter 50 between each ventilation groove 56 is threaded with threads 60. Each thread 60 is angled and shaped so as to facilitate insertion of the connection adapter 50 into an endotracheal tube by means of a longitudinally directed force applied to the adapter, but to exert a resistive force against the removal of connection adapter 50 from an endotracheal tube in opposition to an oppositely directed longitudinally applied force. Alternatively, the adapter may be screwed into place, and unscrewed, as desired. The conical nature of the connection adapter 50 permits the tube retainer 48 to fit securely within the opening of a variety of endotracheal tubes, ranging from standard size No. 6 through standard size No. 8 tubes. The size and shape may be adapted as desired to accommodate larger and/or smaller tubes. As the tube retainer 48 is inserted within the opening of an endotracheal tube, the increasing exterior diameter of the connection adapter 50 prevents insertion beyond a certain point, limited by the interior diameter of the endotracheal tube.

The connection adapter 50 is secured at its base to a disk-shaped adapter base 62. Stylet rod 52 is a semi-rigid, circular cross-section rod. The length of stylet rod 52 is sufficient to traverse the distance between a point external to a patient's oral cavity and the laryngeal opening. During the insertion of the rod retainer 48 within an endotracheal tube or related medical instrument, the end of stylet rod 52, external to the oral cavity, consists of a softer stylet cap 68. Of course, rod 52 may be used separately as an intubating stylet for direct visualization by unscrewing connector adapter 50 from rod 52 and placing cap 68 into the trachea directly. The soft cap 68 is designed and configured to reduce potential tracheal trauma when used as an intubating stylet.

Figures 8, 9, 10, 11:
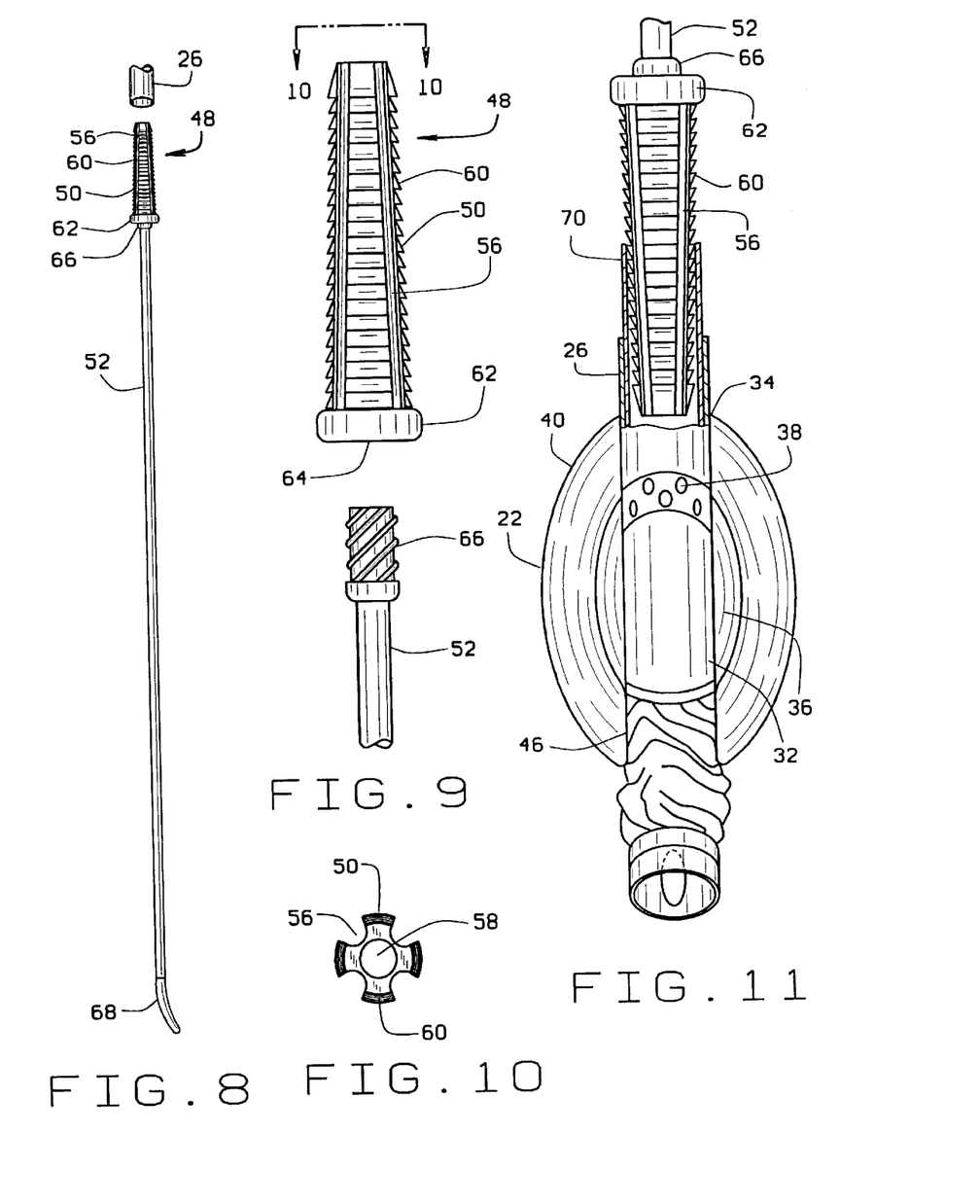
FIG. 8 is a plan view of the endotracheal tube retainer, illustrating the soft cap portion.
FIG. 9 is a plan view of the endotracheal tube retainer, illustrating the separation of the tube retainer body from the connection adapter.
FIG. 10 is a front view of the distal end of the connection adapters, illustrating the air-flow grooves.
FIG. 11 is a plan view of the laryngeal mask of the present invention during use, showing interaction with an endotracheal tube and the endotracheal tube retainer.
Figure 12:
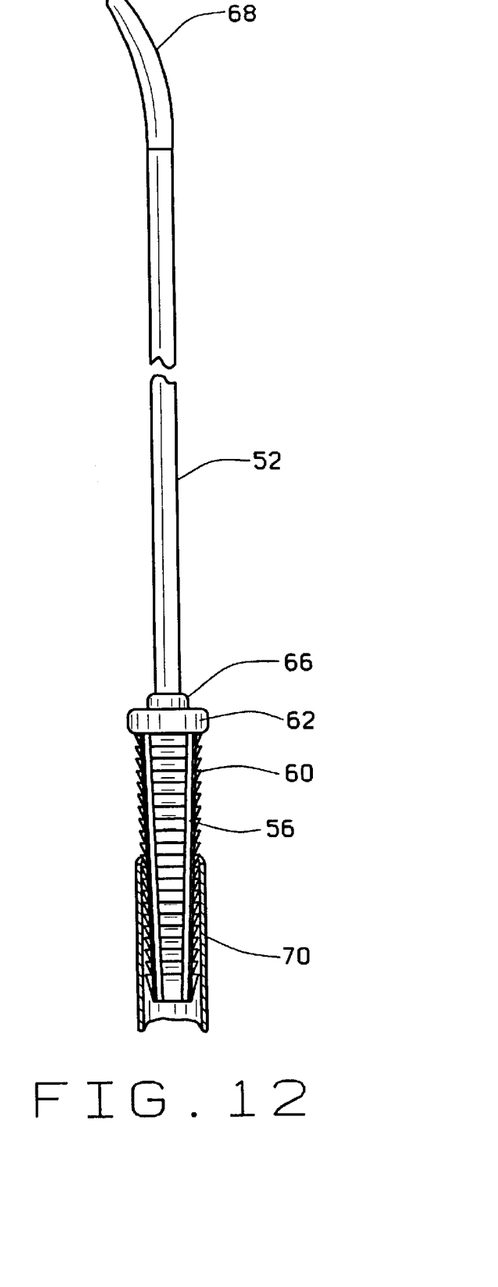
FIG. 12 is a plan view of endotracheal tube retainer during use, illustrating proper position of the tube retainer within an endotracheal tube.
Figure 13:
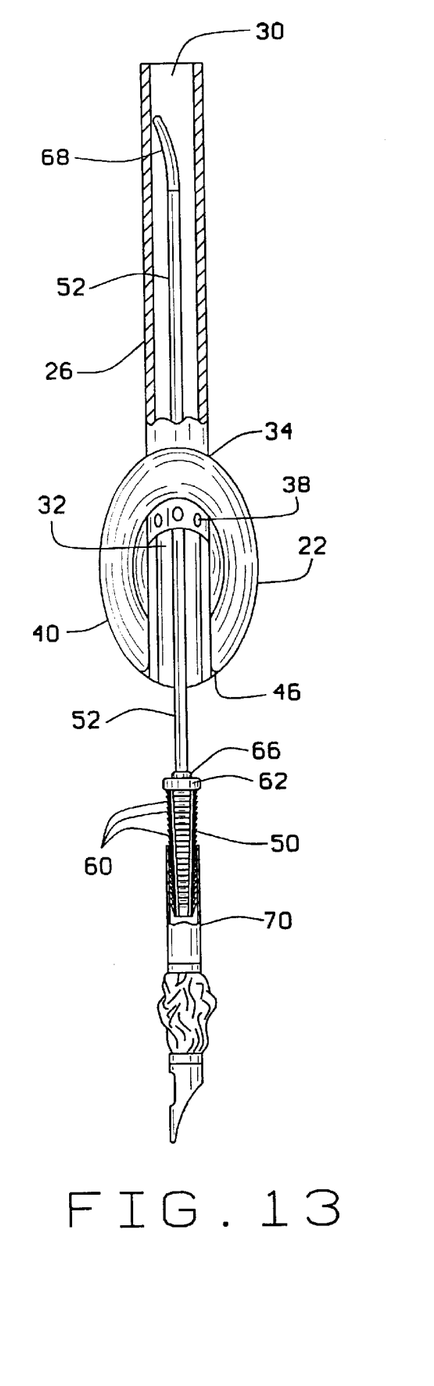
FIG. 13 is a plan view of the laryngeal mask during removal, illustrating the operation of the endotracheal tube retainer.

FIGS. 11–13 illustrate the use of the tube retainer 48 during removal of an laryngeal mask 20. As described above, the use of a tube retainer 48 prevents the displacement of any inserted endotracheal tubes during removal of the laryngeal mask 20. The connection adapter 50 of tube retainer 48 is secured to the stylet rod 52 and passed through the respiratory tube 26. The connection adapter 50 partially enters the proximal opening of the inserted endotracheal tube 70 as shown in FIG. 11. The length of the stylet rod 52 is sufficient to extend beyond the oral cavity after insertion within the endotracheal tube 70, allowing manipulation of the tube retainer as needed to ensure a secure insertion. As shown in FIG. 13, the laryngeal mask 20, may then be removed from the oropharynx without dislodging the endotracheal tube 70 by sliding the laryngeal mask 20 along the tube retainer 48. Tube retainer 48 allows force to be exerted through the stylet rod 52 and connection adapter 50 on the endotracheal tube 70, resisting the tendency of the endotracheal tube 70 to withdraw from the laryngeal opening as the laryngeal mask 20 is removed. Once clear of the oral cavity, the laryngeal mask 20 is simply slid over the stylet cap 68 on the tube retainer 48, allowing the endotracheal tube to remain in place within the patient's laryngeal opening. The stylet is then removed by unscrewing it from the endotracheal tube.

Figure 14:
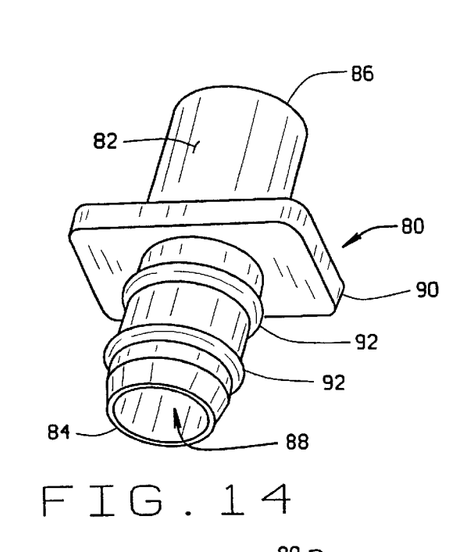
FIG. 14 is a plan view of the adapter of the present invention illustrating the first end having an elliptical cross-section and ribs disposed therein, the wall portion, and the second end having a circular cross-section.
Figure 15A:
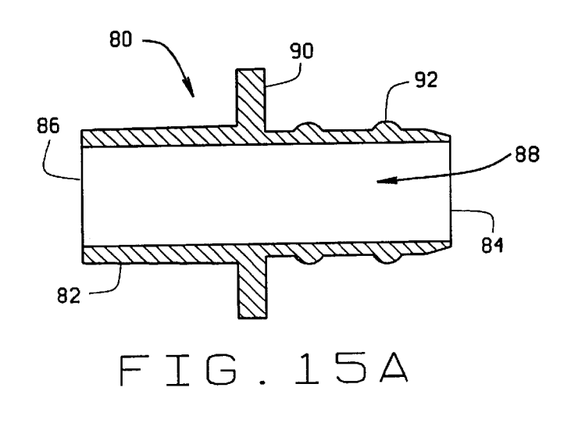
FIG. 15A is a side cross-sectional view of the adapter of FIG. 14.
Figure 15B:
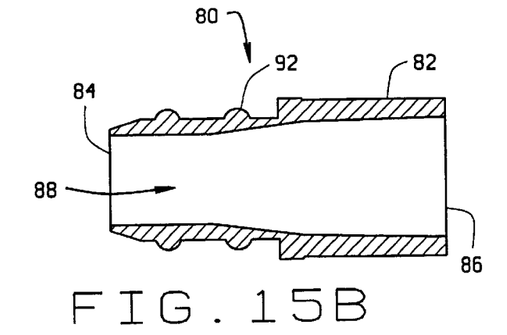
FIG. 15B is a top cross-sectional view of the adapter of FIG. 14.
Figure 15C:
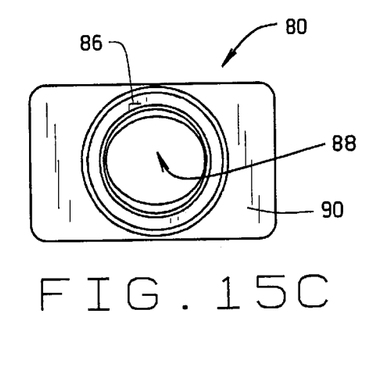
FIG. 15C is a front view of the adapter, illustrating the gradual reduction in inside diameter between the first and second ends of the adapter.

In FIGS. 14 and 15, laryngeal mask 20 is connectable to a variety of medical instruments or devices, for example, lung ventilation machines having connecting tubes that have substantially circular or conical shaped cross-sections, using an adapter 80. Referring to FIGS. 14–15, the attachment end 28 (which has an elliptical cross-section, see FIG. 1A) of laryngeal mask 20 may be fitted with adapter 80 to facilitate connection to tubing of a different cross-section or configuration. During use, adapter 80 is connected to the attachment end 28 and other tubing, for example tubing from lung ventilation machines, by a friction fit.

Adapter 80 is comprised of a body 82 having a first end 84, a second end 86 and a passage 88 therethrough. First end 84 has an elliptical cross-section for communication with the attachment end 28 of respiratory tube 26 (see FIG. 1), or any other tubing having an elliptical cross-section. The outside diameter of the first end 84 is of sufficient diameter to facilitate secure attachment to the attachment end 28 or other tubing thereby forming a fluid-tight connection when adapter 80 is inserted. The body 82 of adapter 80 further includes a second end 86 having a circular cross-section. During use, second end 86 is inserted into tubing from a pre-selected medical device and held in place by a friction fit. In most cases, such tubing has a circular cross-section. Second end 86 is of sufficient outside diameter to form a fluid-tight connection with pre-selected tubing, which is beneficial to ensure proper ventilation of the patient. In one alternate embodiment, the outside diameter of the second end 86 is in the range of between about 15 mm to about 15½ mm to facilitate fitting onto standard tubing from anesthetic medical devices. As illustrated best in FIGS. 15B and 15C, body 82 gradually transitions from the first end 84 having a substantially elliptical cross-section to the second end 86 having a substantially circular cross-section, such that the first end 84 has a smaller inside diameter than the second end 86 and preferably the diameter tapers therebetween. Accordingly, the outside diameter of first end 84 is slightly smaller than the outside diameter of second end 86.

Optionally, a wall 90 is disposed on the body 82 of adapter 80. The location of the wall 90 is not critical. However, in the embodiment shown, wall 90 is disposed substantially centrally between the first end 84 and the second end 86 of body 82 and includes the aforementioned passage 88 therethrough. The wall is adapted to enable the fitting of medical instruments or devices onto the first end 84 and second end 86 of adapter 80. Accordingly, the wall may be any size or shape suitable to enable the fitting of medical instruments or devices on adapter 80. Examples of shapes and sizes that are suitable for fitting of medical instruments or devices on adapter 80 include, but are not limited to disk, rectangle, circular and square shapes. During use, the wall 90 is held between the fingers and utilized to hold the adapter 80 stationary while a user maneuvers tubing onto and off of each of the first end 84 and the second end 86 of adapter 80. The wall 90 may optionally also create a seal between the attached tubing and the adapter 80.

In one embodiment, at least one raised rib 92 is disposed circumferentially around an external portion of the first end 84 for positioning of tubing about the end 84. The ribs 92 are adapted for positioning and retention of the attachment end 28 of respiratory tube 26 or other tubing into the adapter 80. Accordingly, any number of raised ribs 92 may be included that are beneficial for positioning or retention of tubing onto the adapter 80. Alternatively, adapter 80 may be attached to attachment end 28 by adhesive or the like.

After the patient has recovered sufficiently, laryngeal mask 20 and any endotracheal instruments or devices can be removed from the patient and adapter 80 can be removed from the attachment end 28 of respiratory tube 26 or any other attached tubing. The adapter 80 can be cleaned and sterilized for subsequent use with another patient or with another patient.

In view of the above, it will be seen that all the objects and features of the present invention are achieved, and other advantageous results obtained. The description of the invention contained herein is illustrative only, and is not intended in a limiting sense.

I claim:

1. A laryngeal mask of the type used to facilitate lung ventilation and the insertion of endotracheal tubes or related medical instruments through a patient's laryngeal opening during general anesthesia, intensive care, or critical patient care, comprising:

an inflatable positioning shield formed to fit within a patient's oropharynx and seal around the circumference of the laryngeal opening, said shield having a recessed front;

a flexible respiratory tube having a distal end, a proximal end, and a lumen defined by a gently curved tubular body of sufficient size to permit passage of endotracheal tubes, and related medical instruments, wherein the flexible respiratory tube has an elliptical cross-section facilitating insertion of the laryngeal mask through the oral cavity and the distal end of said tube is contained within the inflatable positioning shield, wherein the cross-section is perpendicular to the longitudinal axis of the tube; and an adapter coupled to said proximal end of said respiratory tube for connection of medical devices or tubing, said adapter comprising a body having a first end, a second end and a passage therethrough, wherein said first end has an elliptical cross-section for communication with said flexible respiratory tube and said second end has a cross-section that differs from the cross-section of the first end, wherein the cross-section is perpendicular to the longitudinal axis of the body.

2. The laryngeal mask of claim 1 wherein said first end of said adapter has an elliptical cross-section for communication with said flexible respiratory tube and said second end has a circular cross-section for attachment of tubing.

3. The laryngeal mask of claim 1 wherein said first end of said adapter includes at least one raised rib disposed circumferentially around an external portion of said first end for positioning and retention of tubing about said end.

4. The laryngeal mask of claim 1 wherein said body of said adapter further comprises a wall disposed between said first end and said second end of said adapter.

5. The laryngeal mask of claim 1 wherein the flexible respiratory tube and the inflatable positioning shield are gently precurved along the same arcuate curve such that minimal bending of the flexible respiratory tube is required during positioning of the laryngeal mask.

6. The laryngeal mask of claim 1 wherein the flexible respiratory tube is composed of a material with a low coefficient of function to facilitate the delivery of endotracheal tubes and related medical instruments through the flexible respiratory tube to the laryngeal opening.

7. The laryngeal mask of claim 6 wherein the material of the flexible respiratory tube can deform radially to allow passage of tubes and related instruments having relatively large circular cross-sections, returning to the original elliptical cross-section shape upon the removal of said tubes and related instruments.

8. The laryngeal mask of claim 1 wherein the distal lumen of the flexible respiratory tube is angled to provide an elongated elliptical channel extending substantially to a distal end of the inflatable positioning shield, said channel serving as a guide for endotracheal tubes and related medical instruments and as a support structure for the inflatable positioning shield, preventing the distal end of said inflatable positioning shield from bending during insertion.

9. The laryngeal mask of claim 1 wherein the distal end of the flexible respiratory tube contained within the recessed front of the inflatable positioning shield is perforated by a plurality of small diameter holes, said small diameter holes providing alternate airflow from the laryngeal opening through the recessed front and flexible respiratory tube in the event the distal lumen is obstructed.

10. The laryngeal mask of claim 1 wherein the tubular body of the flexible respiratory tube is of sufficient length to permit the proximal end to be disposed adjacent, but external to, the oral cavity and the distal end to be disposed adjacent and external to the laryngeal opening.

11. The laryngeal mask of claim 1 wherein the inflatable positioning shield is inflatable with air to form an essentially gap-free enclosure surrounding the laryngeal opening.

12. The laryngeal mask of claim 11 wherein the inflatable positioning shield is generally ovoid in shape after inflation, contoured to the anatomical structures found in the oropharynx region.

13. The laryngeal mask of claim 1 wherein the inflatable positioning shield is secured in art air-tight manner to the respiratory tube.

14. The laryngeal mask of claim 1 wherein the recessed front or the positioning shield is in fluid communication with the distal end of said flexible respiratory tube.

15. The laryngeal mask of claim 1 wherein the inflatable positioning shield is of sufficient size to enclose the laryngeal opening.

16. A laryngeal mask of the type used to facilitate lung ventilation and the insertion of endotracheal tubes or related medical instruments through a patient's laryngeal opening during general anesthesia, intensive care, or critical patient care, comprising:

an inflatable positioning shield formed to fit within a patient's oropharynx and seal around the circumference of the laryngeal opening, wherein the inflatable positioning shield has a recessed front;

a flexible respiratory tube having a distal end, a proximal end, and a lumen extending therebetween, said distal end terminating within the inflatable positioning shield such that tubes and instruments passing through the flexible respiratory tube will be directed into the laryngeal opening, said flexible respiratory tube having an elliptical cross-section facilitating insertion of the laryngeal mask through the oral cavity, wherein the cross-section of the tube is perpendicular to the longitudinal axis of the tube; and an adapter coupled to said proximal end of said respiratory tube for connection of medical instruments or devices, said adapter comprising a body having a first end that has an elliptical cross-section, a second end that has a circular cross-section, a wall member disposed substantially centrally between said first end and said second end and a passage therethrough, wherein said first end has an elliptical cross-section including at least one raised rib disposed circumferentially around an external portion of said first end for positioning of tubing, wherein the cross-sections of the ends are perpendicular to the longitudinal axis of the body.

* * * * *